(12) United States Patent
Garripoli

(10) Patent No.: US 9,268,905 B2
(45) Date of Patent: Feb. 23, 2016

(54) METHODS AND SYSTEMS FOR DETERMINING, MONITORING, AND ANALYZING PERSONALIZED RESPONSE VARIABLES USING BRAIN WAVE FREQUENCY DATA AND INTERACTIVE MULTIMEDIA DISPLAY

(71) Applicant: WujiTech, Inc., Kapaa, HI (US)

(72) Inventor: Francesco Garri Garripoli, Kapaa, HI (US)

(73) Assignee: WujiTech, Inc., Kapaa, HI (US)

( * ) Notice: Subject to any disclaimer, the term of this patent is extended or adjusted under 35 U.S.C. 154(b) by 379 days.

(21) Appl. No.: 13/735,745

(22) Filed: Jan. 7, 2013

(65) Prior Publication Data
US 2013/0179087 A1  Jul. 11, 2013

Related U.S. Application Data

(60) Provisional application No. 61/584,158, filed on Jan. 6, 2012.

(51) Int. Cl.
| | |
|---|---|
| G06F 19/00 | (2011.01) |
| A61B 5/0476 | (2006.01) |
| G06F 3/01 | (2006.01) |
| A61B 5/00 | (2006.01) |
| A61B 5/048 | (2006.01) |

(52) U.S. Cl.
CPC ............... G06F 19/30 (2013.01); A61B 5/048 (2013.01); A61B 5/742 (2013.01); G06F 3/015 (2013.01); A61B 2560/0487 (2013.01)

(58) Field of Classification Search
CPC .............. A61B 5/742; A61B 5/048; A61B 2560/0487; G06F 3/015; G06F 19/30
See application file for complete search history.

(56) References Cited

U.S. PATENT DOCUMENTS

2009/0083129 A1*  3/2009  Pradeep et al. ................. 705/10

* cited by examiner

*Primary Examiner* — Christine H Matthews
*Assistant Examiner* — Joshua D Lannu
(74) *Attorney, Agent, or Firm* — Finnegan, Henderson, Farabow, Garrett & Dunner, LLP

(57) ABSTRACT

A computer-implemented method for monitoring one or more response variables in response to a media segment using brain wave frequency data includes displaying a media segment to a user. The media segment includes one or more embedded flags to flag one or more positions of the media segment. The method further includes acquiring brain wave frequency data of the user, acquiring amplitude data of the acquired brain wave frequency data in one or more frequency bands; and determining one or more response variables in response to the acquired amplitude data of the acquired brain wave frequency data correlating to flagged positions of the media segment.

8 Claims, 10 Drawing Sheets

METHODS AND SYSTEMS FOR DETERMINING, MONITORING, AND ANALYZING PERSONALIZED RESPONSE VARIABLES USING BRAIN WAVE FREQUENCY DATA AND INTERACTIVE MULTIMEDIA DISPLAY

CROSS REFERENCE TO RELATED APPLICATIONS

This application claims the benefit of priority of U.S. Provisional Application No. 61/584,158, filed Jan. 6, 2012, the entire contents of which are incorporated herein by reference.

FIELD

Example embodiments relate to systems and methods that monitor and interpret brain activity, and in particular to a method and system for determining, monitoring, and analyzing personalized response variables using brain wave frequency data and an interactive multimedia display.

BACKGROUND

In general, electroencephalography (EEG) is the recording of a brain's electrical activity along the scalp. An EEG is generally divided into five different frequency bands, delta (up to 4 Hz), theta (4-7 Hz), alpha (8-12 Hz), beta (12-30 Hz), and gamma (30-100 Hz). As EEG equipment has advanced over time these frequency bands began to be associated with certain activities or brain states. For example, in neurology, a diagnostic application of EEG is in the case of epilepsy, as epileptic activity can create clear abnormalities on a standard EEG study. Additionally, a secondary clinical use of EEG is in the diagnosis of coma, encephalopathies, and brain death.

Currently, methods of interpreting EEG frequency data are limited to analysis of a subject's results well after the monitoring session has completed. Additionally, the analysis of the results are typically are not interactive. Moreover, while there are methods for monitoring brainwave activity in real time, for example, an MRI, such methods require an expert to interpret the brain wave frequency data. Additionally, the patient/subject typically does not have access to the data for feedback or follow-up.

SUMMARY

According to a first aspect, the present disclosure provides a computer-implemented method for monitoring one or more response variables in response to a media segment using brain wave frequency data. The method may include displaying a media segment to a user. The media segment may include one or more embedded flags to flag one or more positions of the media segment. The method may further include acquiring brain wave frequency data of the user, acquiring amplitude data of the acquired brain wave frequency data in one or more frequency bands; and determining one or more response variables in response to the acquired amplitude data of the acquired brain wave frequency data correlating to flagged positions of the media segment.

According to another aspect, the present disclosure provides an apparatus for monitoring one or more response variables in response to a media segment using brain wave frequency data. The apparatus may include a monitor for displaying a media segment. The media segment may include one or more embedded flags to flag one or more positions of the media segment. The apparatus may further include a device for acquiring a user's brain wave frequency data, and at least one or more processors configured to acquire amplitude data of the acquired brain wave frequency data in one or more frequency bands, and determine one or more response variables in response to the acquired amplitude data of the acquired brain wave frequency data correlating to flagged positions of the media segment.

According to a further aspect, the present disclosure provides a system for monitoring one or more response variables in response to a media segment using brain wave frequency data. The system may include an interface module for displaying a media segment to a user. The media segment may include one or more embedded flags to flag one or more positions of the media segment. The system may further include a brain frequency module for acquiring the brain wave frequency data in one or more frequency bands while the user is viewing the media segment, a data processing module for acquiring amplitude data of the acquired brain wave frequency data in one or more frequency bands, and determine one or more response variables in response to the acquired amplitude data of the acquired brain wave frequency data correlating to flagged positions of the media segment, and a storage module for storing the media segment.

According to a further aspect, the present disclosure provides a system for monitoring brain waves. The system may include an interface module configured to display a media segment to a user. The media segment may include integrated logic, for example, an algorithm. The algorithm may be used to monitor brain wave frequency data, for example, to determine whether an amplitude of the brain wave frequency data in certain frequency bandwidth passes a predetermined threshold. If it does, the integrated logic may cause a processor to generate a signal, e.g., a question for a user. The system may further include a brain frequency module configured to acquire brain wave frequency data in one or more frequency bands while the user is viewing the media segment, and a data processing module configured to adjust displaying of the media segment according to the acquired brain wave frequency data and the integrated logic.

BRIEF DESCRIPTION OF THE DRAWINGS

Reference will now be made to the accompanying drawings showing example embodiments of the present application, and in which.

DESCRIPTION OF EXAMPLE EMBODIMENTS

Reference will now be made in detail to the present exemplary embodiments illustrated in the accompanying drawings. Wherever possible, the same reference numbers will be used throughout the drawings to refer to the same or like parts.

Figure 1:
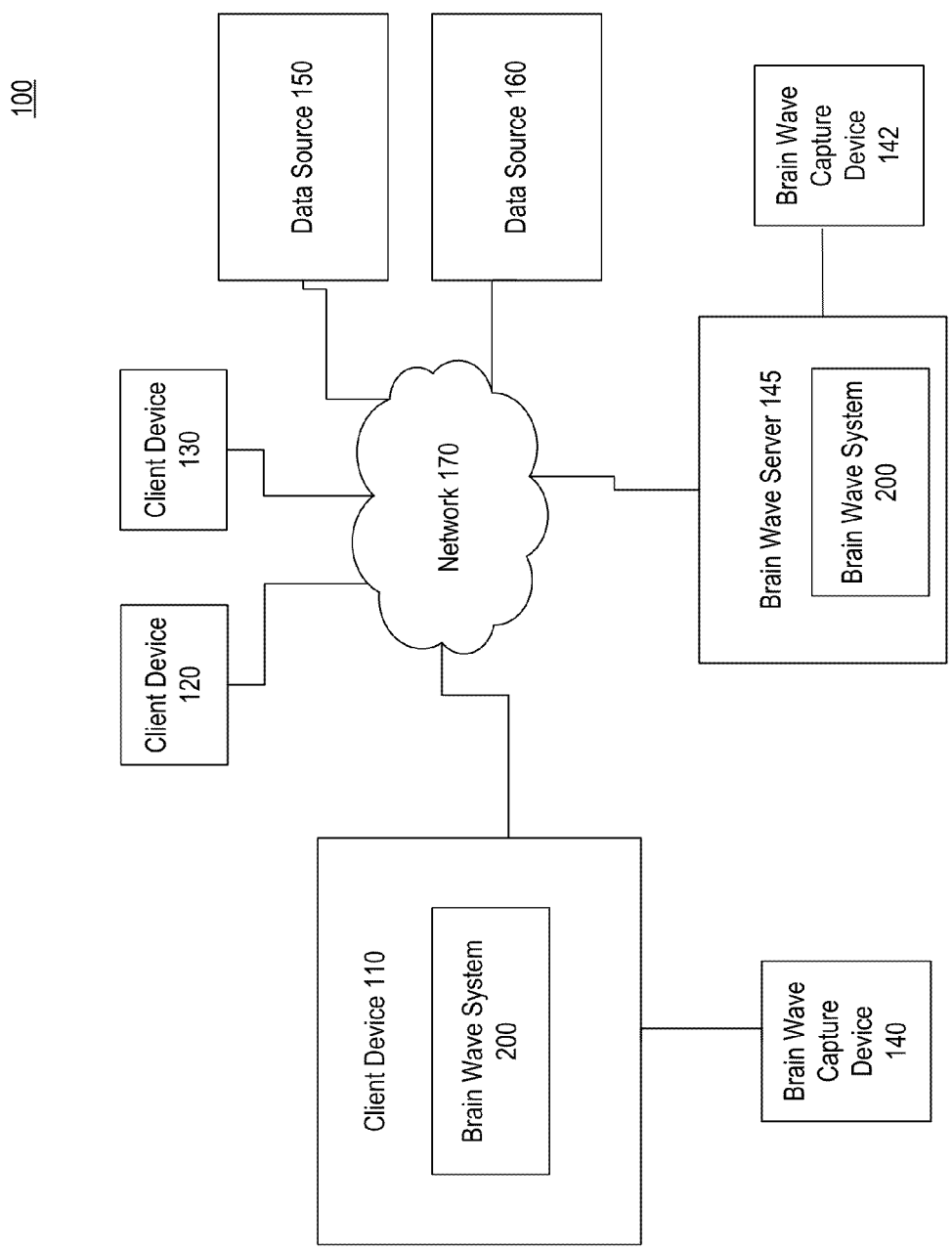
FIG. 1 shows, in block diagram form, an example system utilizing a brain wave system.

FIG. 1 is a block diagram depicting an exemplary system 100 for determining, monitoring, and analyzing personalized response variables to an enhanced media segment using brain wave frequency data. The system 100 may include client devices 110, 120, and 130, brain wave capture devices 140 and 142, brain wave server 145, data sources 150, and 160, network 170, and a brain wave system 200.

Brain wave capture devices 140 and 142 may embody any device that allows for electroencephalography (EEG), and in particular is able to measure the frequency bands, delta, theta, alpha, beta, gamma, mu, or some combination thereof. For example, brain wave capture devices 140 and 142 may embody NEUROSKY's MindWave device, MindBand device, or MindSet device. Brain wave capture device 140 is coupled to client terminal 110 such that it provides brain wave frequency data to brain wave system 200. Additionally, in some embodiments, brain wave capture device 142 may be coupled to brain wave server 145 such that it provides brain wave frequency data to brain wave system 200.

One or more client devices 110, 120, and 130, may be coupled to the brain wave system 200 and brain wave server 145, via the network 170 or some other coupling. In some embodiments, client devices 110, 120, and 130, may be coupled wirelessly to network 170 using one or more wireless access points (not shown). Client devices 110, 120, and 130, may be equipped for Wi-Fi communications. Client device 110 is coupled to brain wave capture device 140. Client devices 110, 120, or 130 may be, for example, personal computers, personal data devices, tablet personal computers, smart mobile phones, laptop computers, or other devices coupled to brain wave system 200 via network 170. Additionally, in some embodiments a user may directly operate brain wave system 200 using brain wave server 145.

Client devices 110, 120, and 130 may include one or more processors (not shown), a memory (not shown), and a data interface (not shown). The processor(s) may be a single or multiple microprocessors, field programmable gate arrays (FPGAs), or digital signal processors (DSPs) capable of executing particular sets of instructions. Computer-readable instructions may be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods may be implemented in hardware components or combinations of hardware and software such as, for example, ASICs, special purpose computers, or general purpose computers. While portions of the specification may only refer to one client device 110, 120, and 130, this is for simplification purposes only and, unless noted otherwise, is not meant to limit the described embodiments in any way.

Data sources 150 and 160 may be any form of database, including a proprietary database containing information about one or more users. Data sources 150 and 160 may be "blogs" or websites, such as social networking websites or news agency websites. Additionally, data sources 150 and 160 may, for example, be search engines like GOOGLE or YAHOO. There may be any number of data sources 150 and 160. While portions of the specification may only refer to only one data sources 150 and/or 160, this has been done for simplification purposes only and, unless noted otherwise, is not meant to limit the described embodiments in any way.

Network 170 may be, for example, the Internet, an intranet, a local area network, a wide area network, a campus area network, a metropolitan area network, an extranet, a private extranet, any set of two or more coupled electronic devices, or a combination of any of these or other appropriate networks.

Brain wave server 145 may include one or more processors (not shown), a memory (not shown), and a data interface (not shown). The processor(s) may be a single or multiple microprocessors, field programmable gate arrays (FPGAs), or digital signal processors (DSPs) capable of executing particular sets of instructions. Computer-readable instructions may be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods may be implemented in hardware components or combinations of hardware and software such as, for example, ASICs, special purpose computers, or general purpose computers. Brain wave server 145 may be implemented on a single computer, or may be distributed across a plurality of computers. Brain wave server 145 may be coupled to multiple data sources, for example, data sources 150 and 160 either via network 170 or via other coupling. Additionally, brain waver server 145 is coupled to client terminal 110 via network 170.

Brain wave server 145, for example, may be part of brain wave system 200 and may be in communication with clients 110, 120, and 130, and data sources 150 and 160, via network 170. Brain wave system 200 may include one or more processors (not shown), a memory (not shown). The processor(s) can be a single or multiple microprocessors, field programmable gate arrays (FPGAs), or digital signal processors (DSPs) capable of executing particular sets of instructions. Computer-readable instructions can be stored on a tangible non-transitory computer-readable medium, such as a flexible disk, a hard disk, a CD-ROM (compact disk-read only memory), and MO (magneto-optical), a DVD-ROM (digital versatile disk-read only memory), a DVD RAM (digital versatile disk-random access memory), or a semiconductor memory. Alternatively, the methods can be implemented in hardware components or combinations of hardware and software such as, for example, ASICs, special purpose computers, or general purpose computers. Brain wave system 200 can be implemented on a mobile device, a computer (for example brain wave server 145), distributed across a plurality of computers or some combination thereof. For example, in some embodiments brain wave system 200 can be distributed across client device 110 and brain wave server 145.

Figure 2:
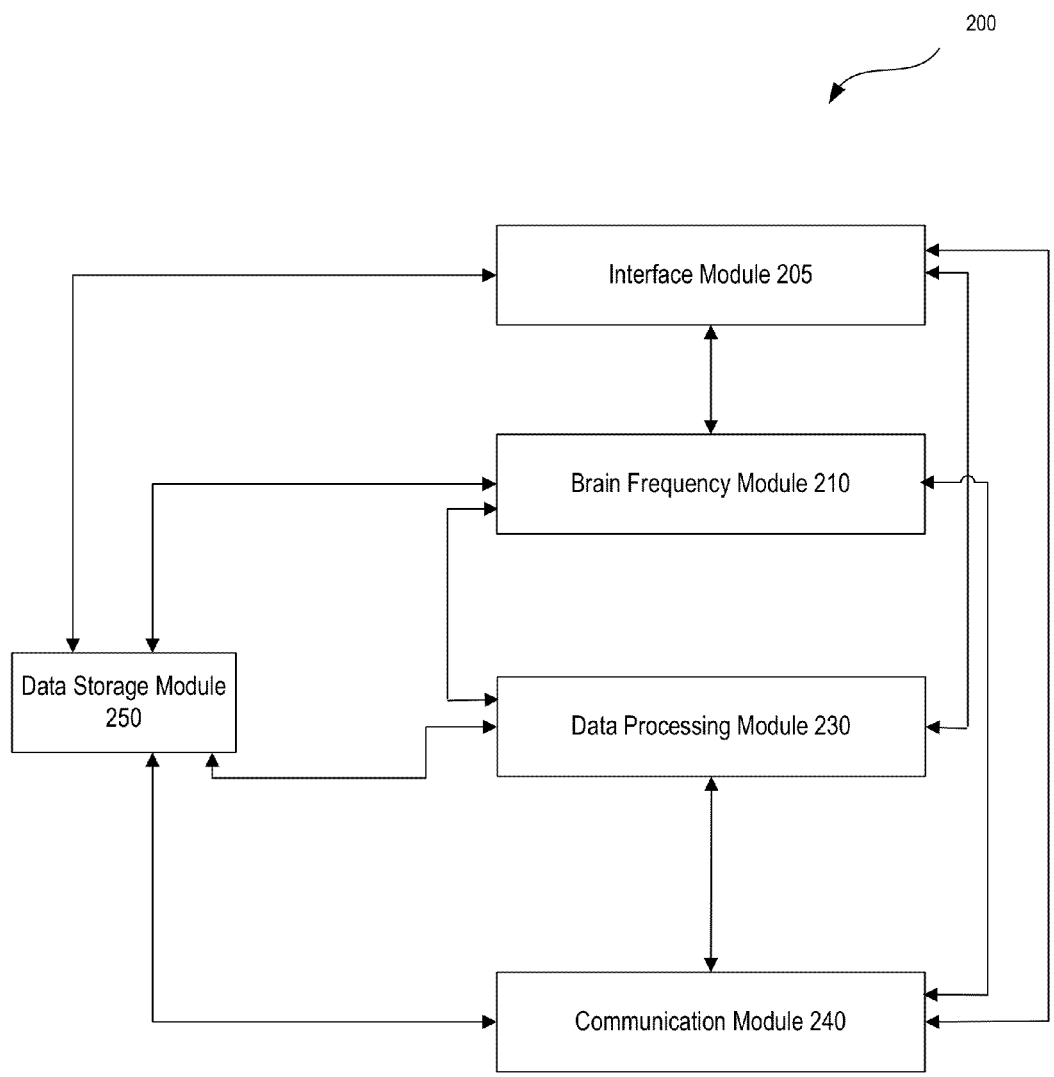
FIG. 2 is a block diagram depicting an example brain wave system.

FIG. 2 is a block diagram depicting exemplary brain wave system 200. Brain wave system 200 may include an interface module 205, a brain frequency module 210, a data processing module 230, a communication module 240, and a data storage module 250. It is appreciated that one or more of these modules can be deleted, modified, or combined together with other modules.

Interface module 205 displays graphical user interfaces (GUIs) allowing a user to interface with brain wave system 200. Interface module 205 displays an enhanced media segment (EMS) GUI (not shown) that allows a user to choose a particular EMS for viewing. An EMS may be an audio or video presentation that has one or more time periods in the EMS flagged. The flagged locations may be associated with expected brain wave frequency data, one or more response variables (e.g., joy, attention, inner calm, etc.), or a combination thereof. The EMSs may be presented to the user in such a way that they can choose an EMS segment based on one or more response variables that they would like to monitor.

Figure 3:
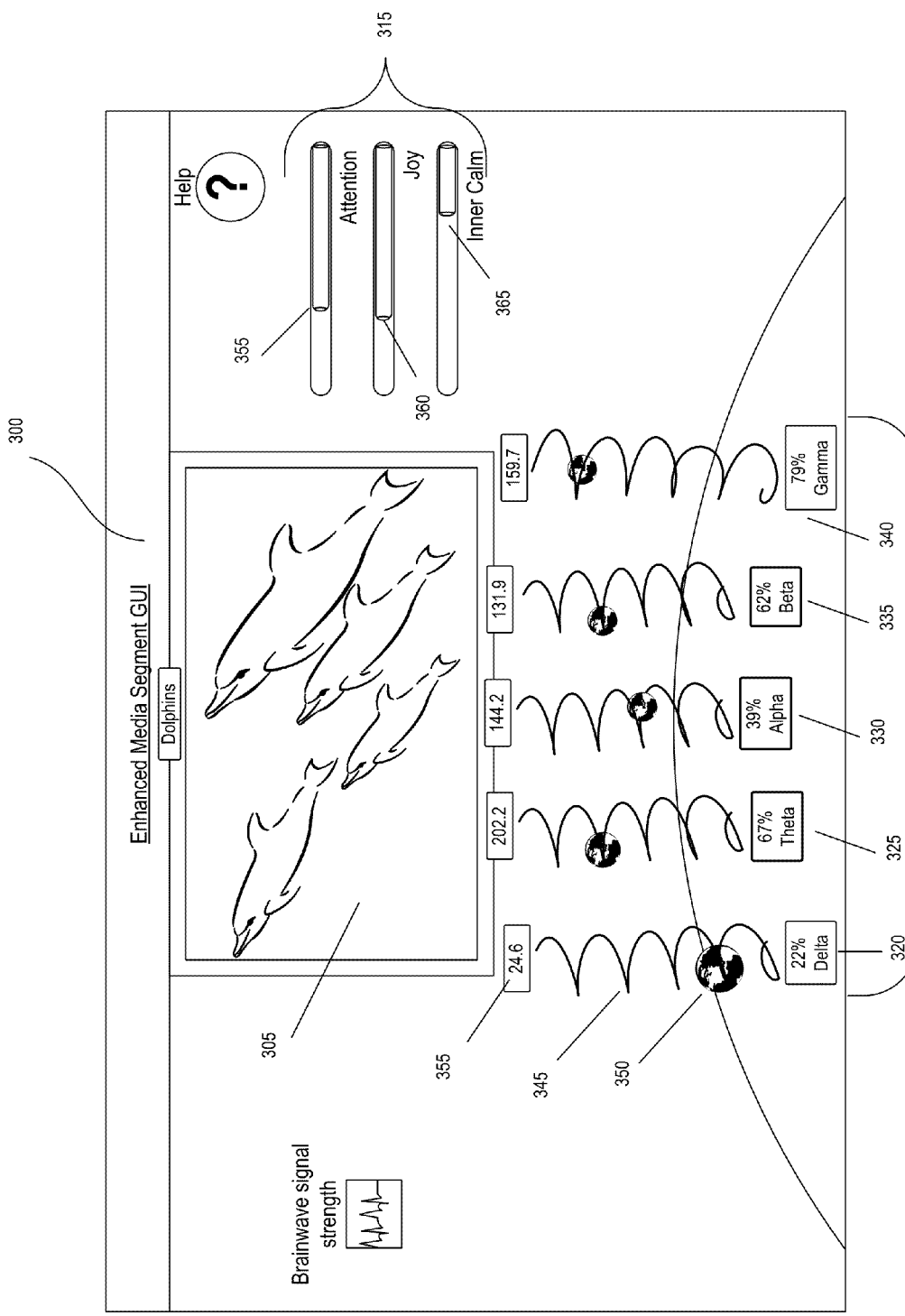
FIG. 3 illustrates an example enhanced media segment graphical user interface.

When a particular EMS is selected for viewing, interface module 205 displays an enhanced media segment graphical user interface (EMS-GUI). FIG. 3 illustrates an example EMS-GUI 300 generated by interface module 205, displaying EMS 305, brain wave frequencies 310, and response variables 315. In this embodiment, EMS 305 is a video of dolphins swimming. EMS 305 may be any video or audio presentation, for example, it may be a product advertisement, related to education (e.g., math problem), etc.

Brain wave frequencies 310 may include delta 320, theta 325, alpha 330, beta 335, gamma 340, mu (not shown), some other frequency band, or some combination thereof. Brain wave frequencies 310 are obtained from a brain wave capture device (e.g., brain wave capture device 140). Measured brain wave frequencies 310 are displayed using a brain wave frequency gauge for each brain wave frequency band of interest. In this embodiment, measured brain wave frequencies 310 are displayed in real time as the user responds to EMS 305. Additionally, the brain wave frequency gauges (e.g., brain wave frequency gauge 345) are shaped like a helix. Each brain wave frequency gauge includes a jewel (e.g., jewel 350) that moves up and down the helix depending on the amount of that particular measured brain wave frequency. For example, delta 320 is at 22% whereas alpha 330 is at 39%. The displayed percentages reflect the proportion of a brain wave frequency to a respective maximum amplitude brainwave amplitude the user can generate. Additionally, each frequency gauge may have an associated box displaying the time the user sustains brainwave output above a predetermined threshold for that particular frequency band. For example, box 355 indicates that the user has maintained brain activity in the delta band above the predetermined threshold (e.g., 50 percent) for 24.6 seconds. In other embodiments, brain wave frequency gauge 345 may be displayed using other means, e.g., a vertical bar, dial type gauges, etc.

EMS-GUI 300 may also display one or more response variables 315. In this embodiment, response variables 315 include attention 355, joy 360, and inner calm 365. One or more response variables are calculated using a lookup table and one or more of the measured brain wave frequencies. The details of the calculation are discussed below in the discussion concerning data processing module 230. In this embodiment, attention 355, joy 360, and inner calm 365 are being determined in real time by brain wave system 200 using measured brain frequency data corresponding to delta 320, theta 325, alpha 330, beta 335, and gamma 340 and a lookup table containing corresponding values for the response variables 315.

After the EMS is terminated, EMS session data is stored as an EMS session entry. The EMS session entry may include, the acquired brain frequency data associated with the viewed EMS, the associated response variables, the actual EMS, the brainwave frequency data and corresponding response variable values contained within the lookup table, the lookup table, or some combination thereof. EMS session data may be stored locally (e.g., client device 110), remotely (e.g., brain wave server 145), or some combination thereof. In some embodiments, EMS-GUI 300 is configured to update a session log with the EMS session entry. The EMS session log may be stored locally, remotely, or a combination thereof.

Figure 4:
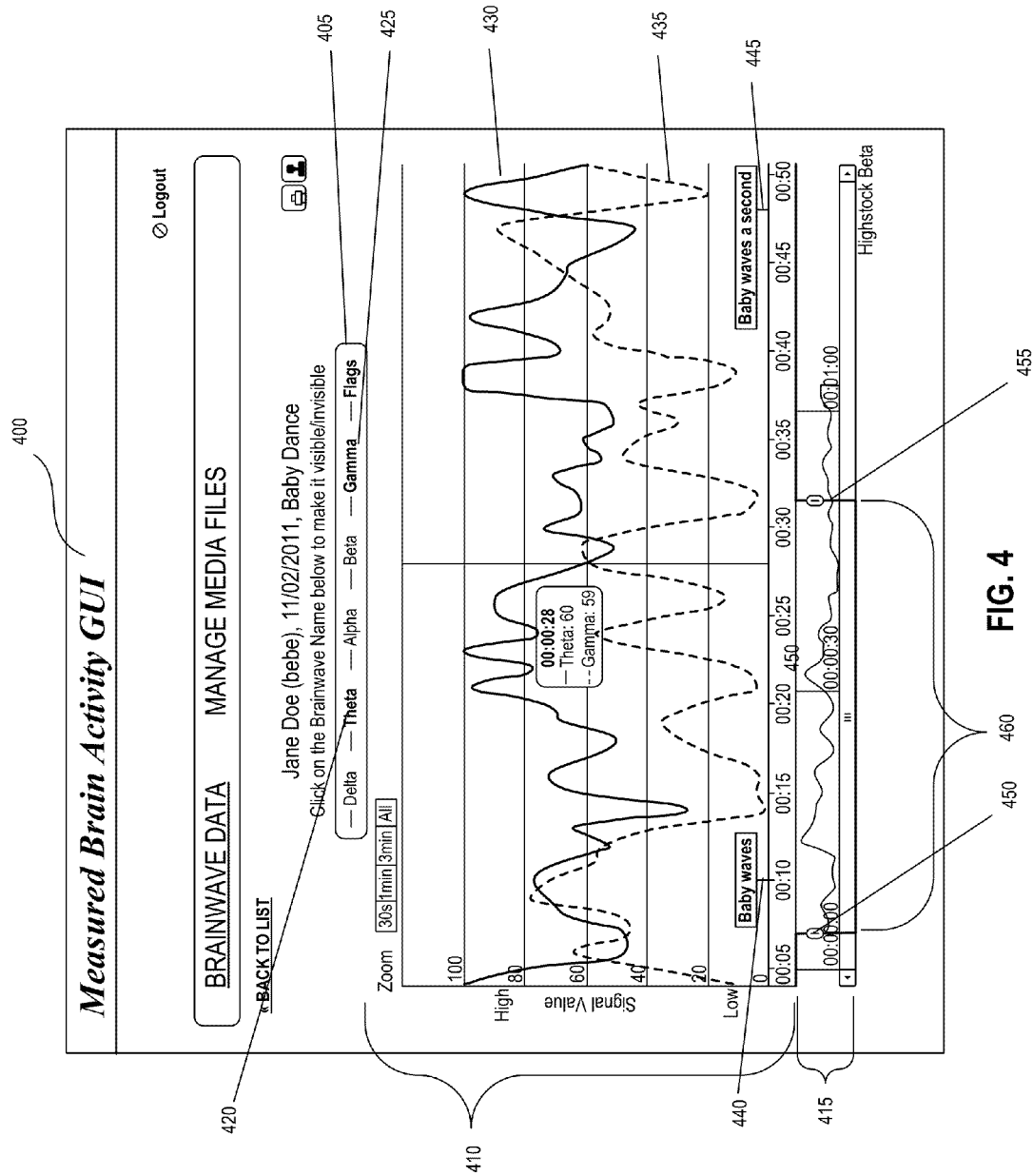
FIG. 4 illustrates an example brain activity graphical user interface.

Once an EMS has been viewed and brain frequency data captured, interface module 205 can generate a measured brain activity graphical user interface configured to display brain wave frequency data measured while the EMS was being viewed. Measured brain wave frequency data may include for example, one or more of frequency bands delta, theta, alpha, beta, gamma, mu, some other frequency band, etc. FIG. 4 illustrates an example measured brain activity graphical user interface (GUI) 400 generated by interface module 205, displaying brain frequency selection tool 405; brain frequency graph 410, and total session view 415. In this embodiment, the displayed data is associated with the EMS titled "Baby Dance."

Brain frequency selection tool 405 allows a user to select for display one or more brain frequencies that were measured during the viewing of the EMS. In this embodiment, theta 420 and gamma 425 have been selected and are displayed in brain frequency graph 410 as curves 430 and 435, respectively. In this embodiment, a user selects the frequency band of interest by simply selecting it within those listed in brain frequency selection tool 405.

Brain frequency graph 410 displays measured brain frequency data selected to be displayed. The horizontal axis of brain frequency graph 410 corresponds to time and the vertical axis corresponds to a signal value (e.g. theta curve 430) as a function of time. In particular, the vertical axis corresponds to signal values at particular points in time associated with the viewed EMS. Measured brain activity GUI 400 also displays one or more flags that are associated with particular time periods of the EMS. Flags may allow a user to monitor their particular brain wave frequency data in response to select audio/visual stimuli occurring at the flagged location (time period) in the EMS. For example, flag 440 corresponds to a location in the EMS where a baby waves, and flag 445 corresponds to another location in the EMS where the baby waves a second time.

Total session view 415 displays the aggregate brain activity that occurred while viewing the EMS. Total session view 415 includes a lower time bracket 450 and an upper time bracket 455 which may be positioned along the horizontal time axis to set a region of interest 460. Accordingly, brain frequency graph 410 displays selected frequencies over the time period indicated by region of interest 460.

The EMS may be coupled with integrated logic, for example, an algorithm. The algorithm may be used to monitor brain wave frequency data, for example, to determine whether an amplitude of the brain wave frequency data in certain frequency bandwidth passes a predetermined threshold. If it does, the integrated logic may cause the data processing module 230 to generate a signal, e.g., a question for a user. Interface module 205 is additionally configured to display an on screen questions or responses after an EMS is viewed. The on screen response may be textual, numerical, a graphical user interface, or some combination thereof. The on screen response obtains feedback from the user pertaining to their experience while watching the EMS. For example, the on-screen response may ask questions like, "what was your level of joy when the baby waved," "how attentive were you when the plane hit the building," etc. In some embodiments, brain wave system 200 is configured to receive answers to one or more on screen response questions via brain wave capture device 140. In other embodiments, brain wave system 200 is configured to receive answers to one or more on screen response questions via the user's manual selection of an answer (e.g., clicking on the answer using a mouse pointer, typing in the response using a keyboard, etc.). Brain wave system 200 is configured to make this information available to EMS developers. Additionally, in some embodiments, brain wave system 200 may use this information to automatically re-calibrate information in the lookup table.

Figure 5:
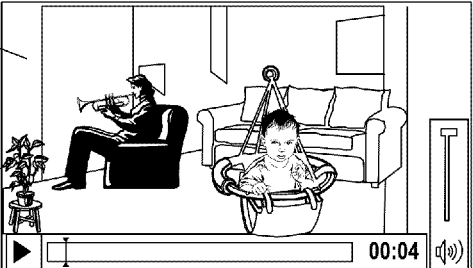
FIG. 5 illustrates an example enhanced media segment developer graphical user interface.

FIG. 5 illustrates an EMS Developer graphical user interface (GUI) 500 generated by interface module 205, displaying EMS 505, personal response list 510, and media flag list 515.

EMS Developer GUI 500 may be configured to allow a user to create, select, modify, or some combination thereof, a particular audio or video file. For example, in this embodiment EMS 505 is a modified video file.

Personal response list 510 displays one or more personal response metrics, e.g., 520, 525, 530, and 535, that a developer may edit after the EMS has been viewed. Each personal response metric is editable, and on screen response GUI 500 allows a user to provide feedback pertaining to one or more response variables (e.g., joy, attention, inner calm, etc.) experienced during the EMS. For example, a developer may edit personal response metric 520 to show that they felt a certain level of joy during the period of time in the EMS. Additionally, brain wave system 200 may make available collected on-screen response data from one or more users. The developer can utilize this data in creating an EMS. This feedback system allows brain wave system 200 to calibrate the values of one or more response variables corresponding to brain wave frequency data in the lookup table. In some embodiments, the user and the developer may be the same entity.

EMS Developer GUI 500 may be configured to allow the developer set flags within the selected file. In some embodiments, the interface may allow a user to associate certain points within the file with predetermined levels of response variables (e.g., joy, attention, inner calm). For example, if the video is a clip of a series of different people, and one of the people is the user's mother. It is likely that there should be a higher level of joy for the period that the user's mother is being displayed. Similarly, if the video clip is of a skyscraper, which a plane crashes into during a specific time period in the video. It is likely that the user's joy would drop suddenly when the plane hit the building. Additionally, it is likely that the user's attention would increase when the plane hit the building. In this way, the developer can pre-calibrate an EMS.

Media flag list 515 displays any flags currently included within EMS 505. In this embodiment, media flag list 515 includes flag 540, flag 545, and flag 550. Flags 540, 545, and 550, are positioned at location times of 10 seconds, 48 seconds, and 85 seconds, respectively, throughout EMS 505. In this embodiment each flag is editable by the developer. For example, a developer may change a flags location time, description, or both. In some embodiments, the developer may additionally be allowed to edit expected values for one or more response variables associated with the flagged location. Additionally, one or more of flags 540, 545, and 550 may be deleted by the developer. Additionally, in some embodiments, one or more additional flags may be added to media flag list 515. In some embodiments (not shown), media flag list 515 may not be displayed.

Additionally, in some embodiments, interface module 205 is also configured to provide a developer response training interface (not shown) to allow a developer to create a training session associated with a personal response training graphical user interface. The developer response training interface may be configured to allow a user to create, modify, select, load, etc., one or more response objects. The one or more of the response objects may include still images, 2D and 3D animations, etc. Additionally, the developer may select which response variables correspond to the uploaded graphics. The developer may use the developer response training interface to create an interactive and education game that displays the one or more objects and allows user interaction with the objects via their acquired brain wave frequencies. In some embodiments, the developer is the same entity as the user.

Figure 6:
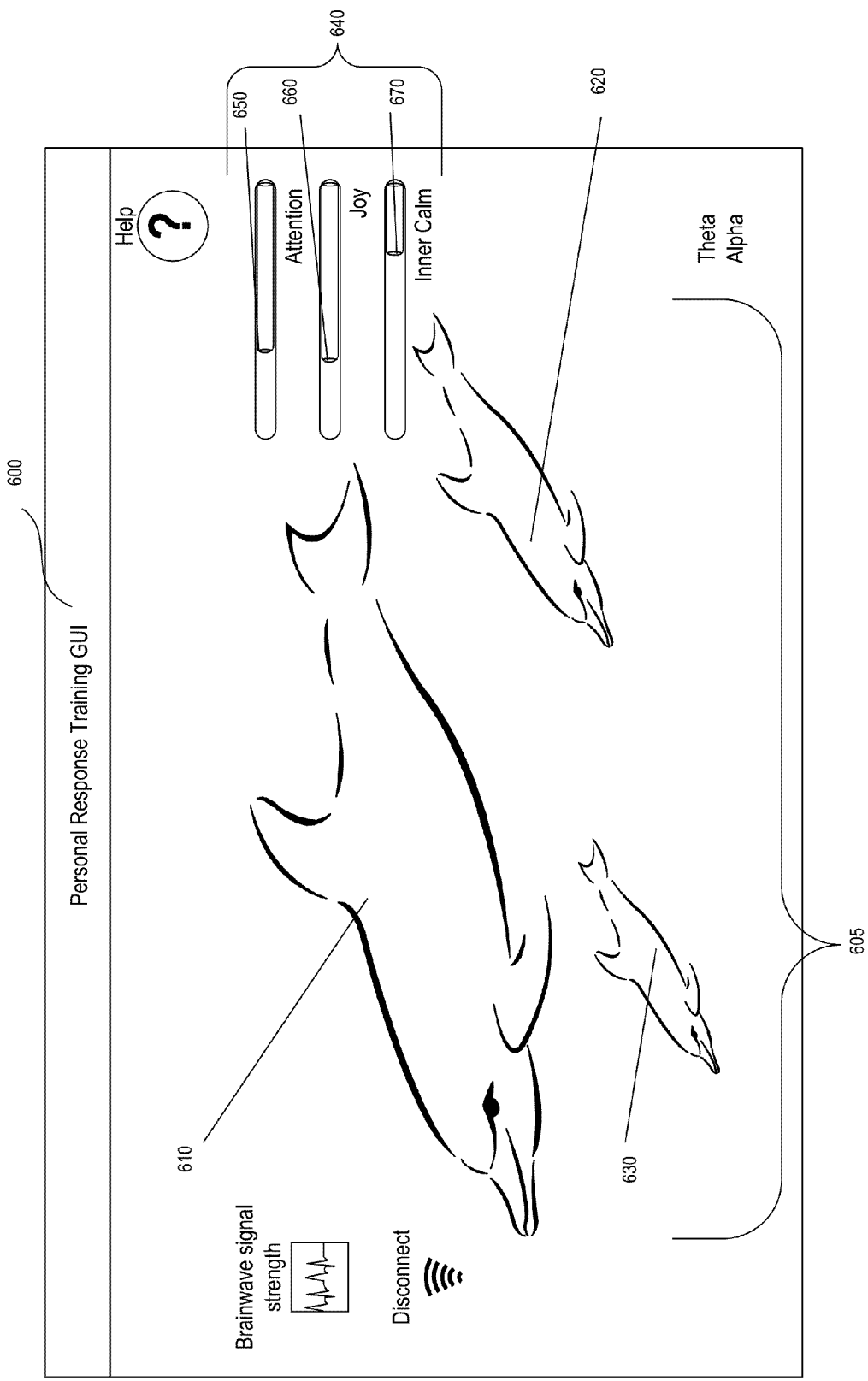
FIG. 6 illustrates an example personal response trainer graphical user interface.

Interface module 205 is additionally configured to display a personal response trainer graphical user interface. The personal response training graphical user interface allows a user to train their brain to respond in certain ways (e.g., achieve a joyful state). The personal response training graphical user interface displays one or more objects that are directed in real time by the user's brainwave frequency data to form an interactive and educational game. FIG. 6 illustrates an example personal response training graphical user interface (GUI) 600 generated by interface module 205, displaying response graphics 605, and response variables 640.

Personal response training GUI 600 may display one or more response variables 640. In this embodiment, response variables 640 include attention 650, joy 660, and inner calm 670. One or more response variables are calculated based on one or more of the measured brain wave frequencies using the lookup table. In this embodiment, attention 650, joy 660, and inner calm 670 are being calculated in real time by brain wave system 200 based on measured brain frequency data of one or more brain wave frequency (e.g., delta, theta, alpha, beta, gamma, mu, etc.).

Display response graphics 605, include response object 610, response object 620, and response object 630. Each response object corresponds to a particular response variable (e.g., joy, attention, inner calm, etc.). In this embodiment, response object 610 corresponds to joy 660, response object 620 corresponds to attention 650, and response object 630 corresponds to inner calm 670. As brain frequency data varies the relative locations of response objects 610, 620, and 630 change. For example, as currently depicted joy 660 is the dominant response, accordingly response object 610 is largest and at the forefront of display response graphics 605. If for example, the measured brain frequency data changed such that inner calm 670 became dominant, response object 630 would move to the forefront and response object 610 would move toward the background. Accordingly, a user can train their brain to achieve a certain response (e.g., joy, attention, inner calm, etc.), by adjusting their thought patterns in such a manner that a response object of interest comes to the foreground and stays in the foreground of display response graphics 605. After the exercise is complete, training session data is stored. Training session data may be stored locally (e.g., client device 110), remotely (e.g., brain wave server 145), or some combination thereof. Additionally, the display response graphics 605 need not be of the same object. Additionally, in some embodiments, the objects may be affiliated with the response variable they are associated with. For example, a response object associate with inner calm may be a Buddha, a response variable associated with joy may be a rainbow, etc. Additionally, in some embodiments, one or more of the response objects may include 2D and 3D animations.

Figure 7:
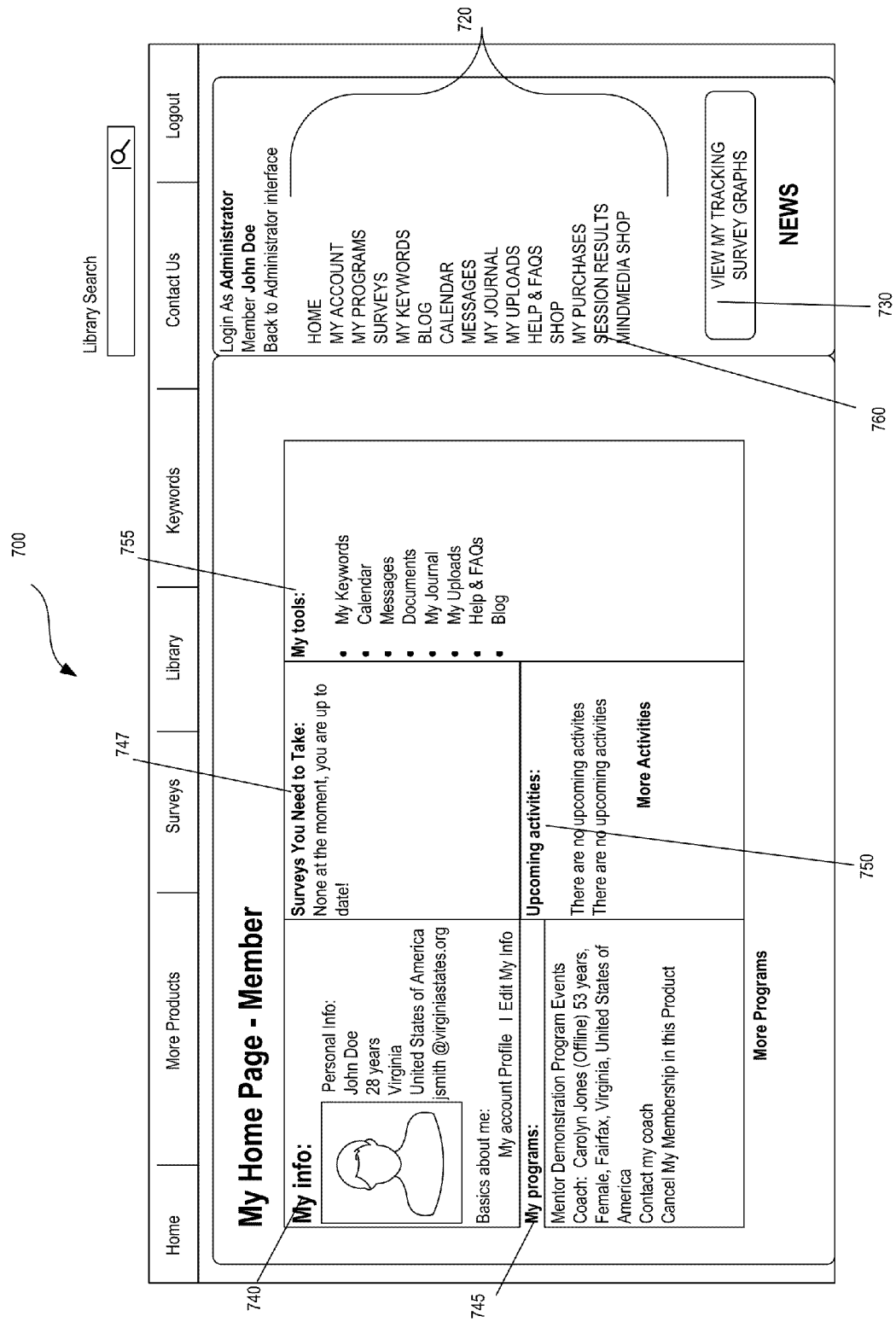
FIG. 7 illustrates an example home page graphical user interface.

Interface module 205 is additionally configured to display a home page graphical user interface. The home page graphical user interface allows a user to access a user journal including data storing information from one or more sessions (e.g., EMS session, training session, etc.) completed by the user. Additionally, in some embodiments, home page graphical user interface with functions of one or more search engines (e.g., data sources 150 and 160), functions of one or more social networking (e.g., data sources 150 and 160), an EMS and training store, and a communication center. The home page may be customized for the user based on their interests. In some embodiments, the user interests are ascertained by information gathered by brain wave system 200. The home page may include functions of a search engine, social networking, content management, survey creation and display, messaging, blogs, ecommerce, brain wave system 200, or some combination thereof. FIG. 7 illustrates an example home page graphical user interface (GUI) 700 generated by interface module 205, displaying a member information area 710, menu commands 720, and survey results button 730. Member information 710 may include personal information 740, my program information 745, suggested surveys 747, upcoming activities 750, user tools 755, or some combination thereof. Personal information 740 may include name, age, address, user name, email address, phone number, one or more images, or some combination thereof. My program information 745 may include information relating to programs affiliated with the user. For example, in this example, the user is affiliated with a mentor demonstration program. Tool list 755 contains a number of links that may be potentially useful to the user. For example, tool list 755 may include links to user keywords, a calendar, a messaging center, stored documents, a journal, prior EMS session data, prior training session data, a help section, a blog, or some combination thereof. In some embodiments, components of member information 710 are customizable by the user.

Menu commands 720 contain a number of links that may be potentially useful to the user. For example, menu commands 720 may include links to home, user account information, user program information, surveys, user keywords, a blog, a calendar, a messaging center, prior EMS session data, prior training session data, a help section, one or more stores, previous purchases, or some combination thereof. In some embodiments, the stores may offer for sale additional EMSs, training modules, software updates, hardware (e.g., brain wave capture device 140), session results 760, or some combination thereof. Session results 760 allows a user to access, for example, an associated EMS session log, an associated training session log, submitted response data, survey data or some combination thereof.

Home page GUI 700 may also be configured to allow users to share their session data with other users of brain wave system 200. For example, home page GUI 700 may allow a user to share EMS session data associated with an EMS of a music video with other users of brain wave system 200. The other users may be able to see, for example, the user's response variables to the particular music video. Similarly, brain wave system 200 may be configured to suggest other users of brain wave system 200 to the user based on their shared EMS session data. For example, brain wave system 200 may suggest that user A contact user B if the response variables to the same or similar EMS sessions are similar.

Figure 9:
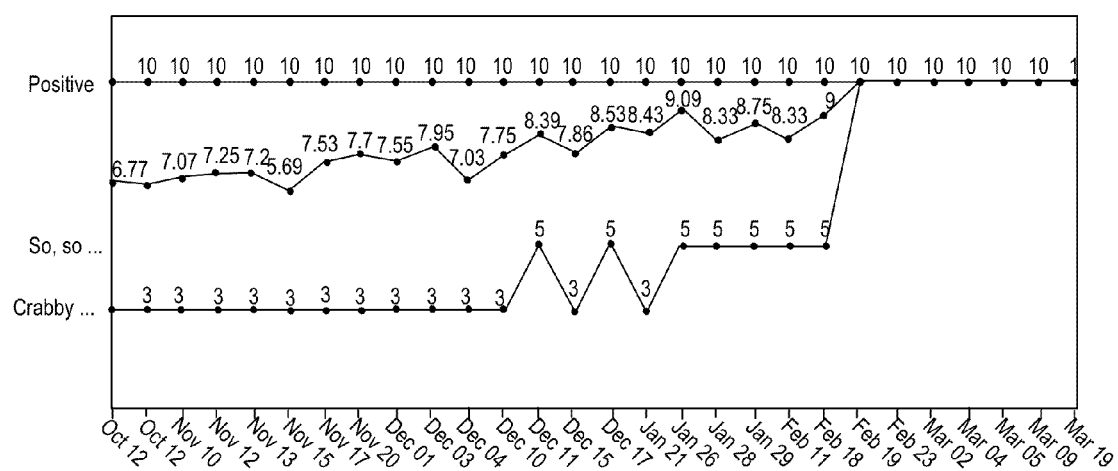
FIG. 9 illustrates an example of survey results.

Referring back to FIG. 2, interface module 205 may be configured to generate and provide one or more surveys to the user. A survey for example may include questions like, "today I would rate my energy level as," "today my health is," "last night I slept between," "today I would say my attitude is," etc. An example survey with results aggregated over time is seen in FIG. 9. In some embodiments, survey data may provide qualitative data that may contribute to the aggregate pool of data that defines communities and social networks of which the user is a member. Additionally, referring back to FIG. 2, in some embodiments, brain wave system 200 may utilize survey data to push information from brain wave system 200 to the user. For example, survey data may suggest that the user would be interested in an EMS of a particular music video. Brain wave system 200 may then suggest the particular EMS to the user, via the homepage GUI 700. Additionally, in some embodiments, survey data can be used to monitor user progress over time. For example, brain wave system 200 may utilize the survey data to track student progress, teacher progress, or a combination thereof, over time. Brain wave system 200 may then analyze the survey data, and suggest courseware which they may find beneficial. For example, if the survey data shows a student's increasing confidence in math. Brain wave system 200 may suggest via homepage GUI 700 math courseware of increasingly difficulty. In some embodiments, the suggested courseware may be available for purchase electronically from an e-store accessible via the user's homepage (e.g., homepage GUI 700).

Additionally, interface module 205 may be configured to update a survey log with the submitted survey data. The survey log may maintain survey data for the user. Additionally, in some embodiments, the survey log may contain data from a plurality of users. In some embodiments, interface module 205 is configured to upload any submitted survey data to a server (e.g., brain wave server 145), that then updates the survey log stored on the server. In other embodiments, the survey is stored locally on the client device (e.g., client device 110), and interface module 205 is configured to update the survey log with the submitted survey data. In some embodiments, brain wave system 200 may be configured to combine one or more session entries with the selected survey response data to create a composite graph.

Figure 10:
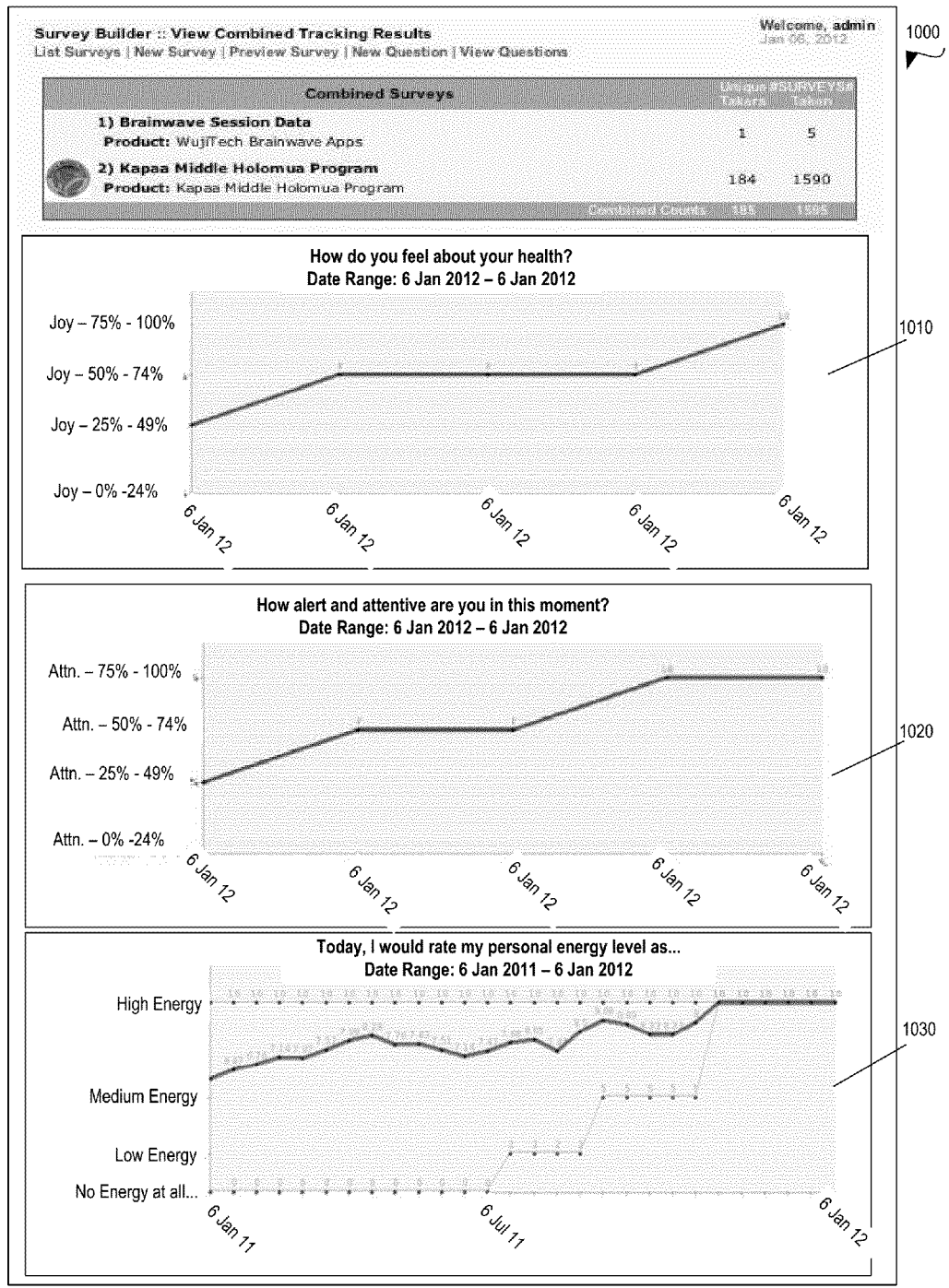
FIG. 10 illustrates an example combined results graphical user interface.

In some embodiments, interface module 205 is additionally configured to display a combined graphical user interface. The combined graphical user interface allows the user to combine qualitative and quantitative data such that it may be displayed together. FIG. 10 illustrates a combined graphical user interface (GUI) 1000. Combined GUI 1000 includes three separate graphs. Graphs 1010 and 1020 are populated with data that is calculated based on the acquired brain frequency data. Graph 1030 is populated with survey data that the user qualitatively selects each day. This combination of quantitative EMS session data with qualitative survey data may be aggregated and tracked over time.

Interface module 205 may be coupled to one or more of brain frequency module 210, data processing module 230; communications module 240, and data storage module 250.

Brain frequency module 210 is a hardware component, a software program, or a combination thereof configured to acquire brain wave frequency data from a user. In particular, brain frequency module 210 is configured to acquire the frequency bands, delta, theta, alpha, beta, gamma, mu, or some combination thereof, in real time while the user is viewing an EMS. Additionally, in some embodiments, brain frequency module 210 is able to acquire the frequency bands, delta, theta, alpha, beta, gamma, mu, or some combination thereof, in real time while the user is viewing a personal response trainer GUI. Additionally, in some embodiments (not shown) brain frequency module 210 includes a brain wave capture device (e.g., brain wave capture device 140). Brain frequency module 210 may be coupled to one or more of interface module 205, data processing module 230, communication module 240, and data storage module 250.

Data processing module 230 is a hardware component, a software program, or a combination thereof configured to calculate one or more response variables based on acquired brain wave frequency data. Data processing module is configured to acquire a user lookup table associated with the user. For example, the lookup table may be downloaded from a server (e.g. brain wave server 145). The lookup table contains brain wave frequency data (e.g., delta, theta, alpha, beta, gamma, mu, some other frequency band, or some combination thereof), and corresponding values for one or more response variables (e.g., joy, attention, inner calm, etc.). In some embodiments, the joy response variable can be defined as 80% gamma (30-100 Hz)+20% Beta (12-30 Hz)+5% Theta (4-7 Hz). Additionally, in some embodiments, the attention response variable can be defined as 75% theta+25% beta. Additionally, in some embodiments, the inner calm response variable can be defined as 50% delta (0.5-4 Hz)+25% theta. In other embodiments, the joy response variable may also be described as "positive", "affirmative", "happy," etc. In these embodiments, the one or more response variables of this invention may range in frequency from 100% gamma to 50% gamma+20% delta+30% alpha (8-12 Hz). In some embodiments, brain wave system 200 actively changes the combinations of brain wave frequencies that correspond to one or more response variables based on feedback from the user. If the user has no EMS session entries in their session log, data processing module 230 is configured to provide a template lookup table containing brain wave frequency data and predicted corresponding values for one or more response variables. Additionally, in some embodiments, the user may manually adjust the combinations of brain wave frequencies contained in the lookup table.

The data processing module 230 is configured to determine the values of the one or more response variables by matching the acquired brain frequency data to corresponding values of the one or more response variables in the lookup table. Data processing module 230 is configured to reference the lookup table to determine one or more response variables for any time segment of the EMS based on the acquired brain frequency data. Additionally, Data processing module 230 is configured to correlate the acquired brain wave frequency data with flagged positions within the viewed EMS that have associated predetermined response values. Data processing module 230 then extrapolates other values of response variables based on the acquired brain wave frequency data and their corresponding predetermined response values. Data processing module 230 is configured to use this information to update the date contained within the lookup table.

Data processing module 230 is configured to further refine the lookup table with feedback information received from the user after viewing an EMS. As discussed above, after an EMS is viewed, the user is allowed to edit their responses, expectations, theoretical concepts, or some combination thereof, specific areas within the EMS. For example, if the predetermined value for a time period T is 70% of maximum joy, however, the user only experienced 30% of maximum joy, and edits the on screen response to reflect his perceived value of joy. Data processing module 230 is configured to adjust its determination for joy based on the measured brain wave frequency data, and update the look up table accordingly.

Additionally, in some embodiments, data processing module 230 is configured to simply store the user feedback. In this embodiment, interface 205 is configured to prompt the user to re-view the EMS without data processing module 230 updating data in the lookup table. As discussed above after each viewing an EMS session entry is created that is used to update the user's session log. Because the data in the lookup table is not being updated, the relationship between the acquired brain wave frequency data and the one or more response variables remains constant. Accordingly, a user may view their session log and obtain feedback in how one or more of the response variables are being affected over time. For example, a user wanting to improve their joy level may view a particular EMS multiple times, each time trying to increase the level of joy by thinking in a specific way. The user's session log may include sessions entries that correspond to each of the EMS viewings, where each session entry depicts the amount of joy achieved.

Data processing module 230 may process the brain wave frequency data at the user device (e.g., client device 110), remote from the user device (e.g., brain wave server 145), or a combination thereof. Data processing module 230 may be coupled to one or more of interface module 205, brain frequency module 210, EMS and training module 230, communication module 240 and data storage module 250.

Communication module 240 is configured to provide one or more remote interfaces with brain wave system 200. For example, communication module 240 is configured to allow a remote user to login into their homepage (e.g., home page GUI 700) from a terminal that does not have brain wave system 200 installed (e.g., client device 120).

Additionally, communication module 240 is configured to transmit EMS data between systems that are part of brain wave system 200. For example, communications module 240 may be configured to stream one or more EMSs from a server (e.g., brain wave server 145) to a remote client (e.g., client device 110). In some embodiments, the remote client downloads the one or more EMSs before displaying them to the user (e.g., as described above with reference to FIG. 3). Similarly, communications module 240 may be configured to stream data associated with personal response training GUI 600. Additionally, communication module 240 may be configured to communicate with one or more search engines and social networking cites (e.g., data sources 150 and 160).

Communication module 240 may transmit brain wave frequency, personalized response data, session entry data (e.g., EMS session, training session, etc.), or some combination thereof, from a user device (e.g., client device 110) to a server (e.g., brain wave server 145), or vice versa. Communication module 240 can be coupled to interface module 205, brain frequency module 210, data processing module 230, and data storage module 250.

Data storage module 250 may comprise a random access memory (RAM), a read only memory (ROM), a programmable read-only memory (PROM), a field programmable read-only memory (FPROM), or other dynamic storage device for storing information and instructions to be used by interface module 205, brain frequency module 210, data processing module 230, and communication module 240. For example, data storage module 250 may store data received by interface module 205, brain frequency module 210, data processing module 230. Data storage module 250 may also include a database, one or more computer files in a directory structure, or any other appropriate data storage mechanism such as a memory. In some embodiments, data storage module 250 is distributed across a plurality of different data storage mechanisms.

The coupling between modules, or between modules and network 170, may include, but is not limited to, electronic connections, coaxial cables, copper wire, and fiber optics, including the wires that comprise network 170. The coupling may also take the form of acoustic or light waves, such as lasers and those generated during radio-wave and infra-red data communications. Coupling may also be accomplished by communicating control information or data through one or more networks to other data devices.

Each of the logical or functional modules described above may comprise multiple modules. The modules may be implemented individually or their functions may be combined with the functions of other modules. Further, each of the modules may be implemented on individual components, or the modules may be implemented as a combination of components. For example, interface module 205, brain frequency module 210, data processing module 230, and communication module 240, may each be implemented by a field-programmable gate array (FPGA), an application-specific integrated circuit (ASIC), a complex programmable logic device (CPLD), a printed circuit board (PCB), a combination of programmable logic components and programmable interconnects, single CPU chip, a CPU chip combined on a motherboard, a general purpose computer, or any other combination of devices or modules capable of performing the tasks of modules 205, 210, 230, 240, and 250. Additionally, in some embodiments, brain frequency module 210 may include a brain wave capture device (e.g., brain wave capture device 140).

Figure 8:
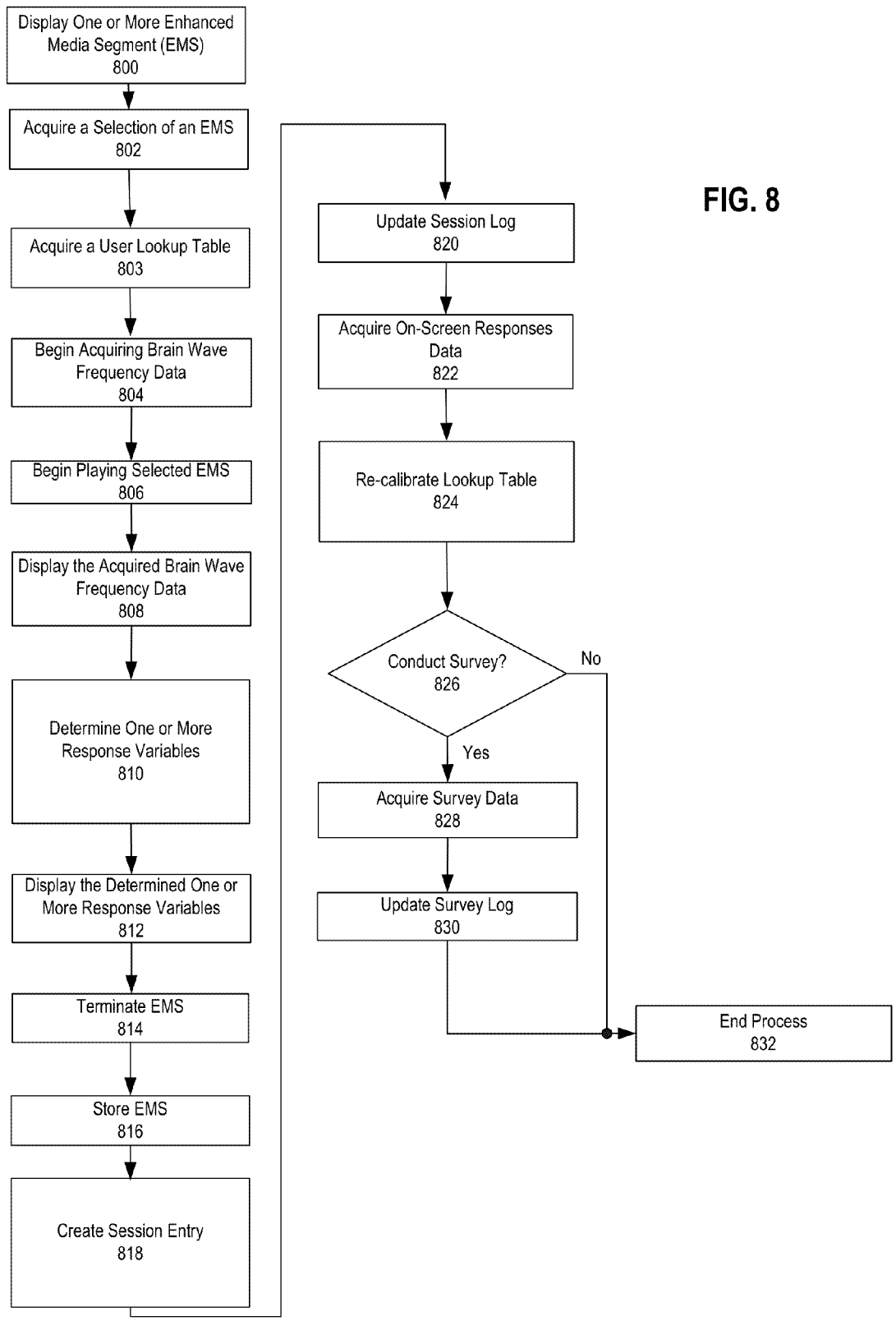
FIG. 8 shows a flowchart representing an example method performed by the brain wave system that facilitates the monitoring of one or more response variables.

FIG. 8 is a flowchart representing an example method performed by a brain wave system that facilitates the monitoring of one or more response variables. While the flowchart discloses the following steps in a particular order, it is appreciated that at least some of the steps can be moved, modified, or deleted where appropriate.

In step 800, brain wave system displays one or more EMSs to the user. The user may then select a particular EMS for viewing. In step 802 the brain wave system acquires the user selection of the EMS.

In step 803, brain wave system acquires a lookup table associated with the user. The lookup table contains brain wave frequency data (e.g., delta, theta, alpha, beta, gamma, mu, some other frequency band, or some combination thereof), and corresponding values for one or more response variables (e.g., joy, attention, inner calm, etc.). In some embodiments, the joy response variable can be defined as 80% gamma (30-100 Hz)+20% Beta (12-30 Hz)+5% Theta (4-7 Hz). Additionally, in some embodiments, the attention response variable can be defined as 75% theta+25% beta. Additionally, in some embodiments, the inner calm response variable can be defined as 50% delta (0.5-4 Hz)+25% theta. In other embodiments, the joy response variable may also be described as "positive", "affirmative", "happy," etc., and may range in frequency from 100% gamma to 50% gamma+20% delta+30% alpha (8-12 Hz). If this is the first time the user has viewed any EMS the brain wave system provides a template lookup table containing brain wave frequency data and predicted corresponding values for one or more response variables.

In step 804, the brain wave system begins acquiring brain wave frequency data from the user. Brain wave frequency data may include delta, theta, alpha, beta, gamma, mu, some other frequency band, or some combination thereof.

In step 806, the brain wave system begins to play the selected EMS. In some embodiments, if this the first time the user has viewed the selected EMS, the brain wave system may stream the EMS from a server (e.g., brain wave server 145) to the client device for viewing. Additionally, in other embodiments, the client device may download the EMS in its entirety prior to viewing. Brain wave system may determine whether this is the first time the user has viewed any EMS by referencing a user session log to determine whether the user has viewed an EMS previously.

In step 808, the brain wave system begins to display one or more frequency bands of the acquired brain wave frequency data. Brain wave system displays in real time the acquired one or more brain wave frequencies using one or more brain wave frequency gauges. Brain wave frequency gauges may be, for example, a helix (see EMS GUI 300), a vertical bar, dial type gauges, etc. In some embodiments, the user may select which brain wave frequencies are displayed. In other embodiments, the specific brain wave frequencies that are displayed are determined by the EMS.

In step 810, the brain wave system determines one or more response variables. The brain wave system determines the values of the one or more response variables by matching the acquired brain frequency data to corresponding values of the one or more response variables in the lookup table.

In some embodiments, the lookup table may be dynamically updated as the EMS is played. The brain wave system determines the values one or more response variables by correlating the acquired brain wave frequency data with one or more flagged positions within the selected EMS. Each of the one or more flagged positions has one or more associated predetermined response values that correspond to particular response variables. Using the acquired brain wave frequency data and the corresponding predetermined response values, the brain wave system extrapolates the values of response variables as a function of the acquired brain wave frequencies. The brain wave system may then update the lookup table with the extrapolated response variable data. As brain frequency data is collected for each flag within the EMS the data within the lookup table is refined. For example, the brain wave system can adjust the combinations of brain frequencies used to determine an associated response variable. Additionally, in some embodiments (not shown), the user may manually adjust the combinations of brain wave frequencies contained in the lookup table.

The brain wave system displays (step 812) the one or more response variables in real time using the acquired brain wave frequency data and the corresponding one or more response variable values contained within the lookup table. Once the EMS terminates (step 814) the brain wave server may store the EMS (816) for future viewing. For example, the brain wave system may store the EMS in the client device's cache or in non-transient storage.

In step 818, the brain wave system creates an EMS session entry. The EMS session entry may include, the acquired brain frequency data associated with the viewed EMS, the associated response variables, the actual EMS, the brainwave frequency data and corresponding response variable values contained within the lookup table, the lookup table, or some combination thereof. In step 820, the brain wave server updates a session log with the EMS session entry. In some embodiments, the EMS session entry is uploaded to a server (e.g., brain wave server 145) that maintains the session log. In this embodiment, the server updates the session log with the uploaded session. Additionally, in some embodiments (not shown), the brain wave system prompts the user to re-view the EMS without updating data in the lookup table.

In step 822, the brain wave system may acquire one or more on screen responses. The on screen response may be textual, numerical, a graphical user interface, or some combination thereof. The on screen response obtains feedback from the user pertaining to their experience while watching the EMS. For example, the on-screen response may ask questions like, "what was your level of joy when the baby waved," "how attentive were you when the plane hit the building," etc. In some embodiments (not shown) the brain wave system collects user feedback data and make this information available to EMS developers.

In some embodiments, the brain wave system may use this adjusted response data to re-calibrate its calculations of one or more response variables contained in the lookup table (step 824). Additionally, the brain wave system may use the adjusted response data to re-calibrate (not shown) the predetermined response values contained within the EMS. In some embodiments (not shown), the user may add, subtract, or modify one or more flags within the EMS.

In step 826, the brain wave system may prompt the user to conduct a survey. Additionally, in some embodiments (not shown), the brain wave system may utilize survey data to push information from the brain wave system to the user. For example, survey data may suggest that the user would be interested in an EMS of a particular music video. The brain wave system may then suggest the particular EMS to the user, via the user's homepage. In some embodiments, the suggested media may be available from an e-store accessible from the user's homepage (e.g., homepage GUI 700). Additionally, in some embodiments (not shown), the brain wave system utilizes the survey data to track student progress, teacher progress, or a combination thereof, over time. The brain wave system then analyzes the survey data, and suggests courseware to the user that may be beneficial. For example, if the survey data shows a student's increasing confidence in math, the brain wave system may suggest via the user's homepage math courseware of increasingly difficulty. If the user elects to not participate in the survey, the process ends (step 832). If the user elects to participate with the survey, the brain wave system will acquire survey response data from the user (828) and update a survey log (step 830). The survey log maintains survey data for the user. Additionally, in some embodiments, the survey log main contain data from a plurality of users. In some embodiments (not shown), the brain wave system may combine one or more session entries with selected survey response data (see, e.g., FIG. 10). The process then ends (step 832).

Additionally, in some embodiments not shown, the moderator control system also transfers conference information to the identified moderator. Conference information can include number of conference participants, identity of conference participants, and roles of conference participants (acting as a moderator or a subgroup moderator).

Certain adaptations and modifications of the described embodiments can be made. Therefore, the above discussed embodiments are considered to be illustrative and not restrictive. Embodiments of the present application are not limited to any particular operating system, mobile device architecture, server architecture, or computer programming language.

What is claimed is:

1. A computer-implemented method for monitoring one or more response variables in response to a media segment using brain wave frequency data of a user, comprising:
   providing a brain wave system configured to display media segments and determine response variables, wherein said system comprises a look up table with correlations between brain wave frequency data and one or more response variables;
   displaying a media segment to the user using the system, wherein the media segment includes one or more embedded flags to flag one or more positions of the media segment, and wherein the one or more embedded flags are associated with expected brain wave frequency data;
   acquiring brain wave frequency data of the user;
   acquiring amplitude data of the acquired brain wave frequency data in one or more frequency bands; and
   determining the one or more response variables using the system, based on the acquired amplitude data of the acquired brain wave frequency data wherein the determining step comprises:
      comparing the acquired amplitude data of the acquired brain wave frequency data to the look up table of brain wave frequency data that contains correlations to one or more response variables;
      correlating the acquired amplitude data of the acquired brain wave frequency data to the one or more response variables on the look table;
      correlating the one or more response variables to flagged positions of the media segment; and
      displaying the one or more response variables to the user on a graphical user interface of the system.

2. The method of claim 1, wherein determining the one or more response variables comprises acquiring values of one or more response variables corresponding to the acquired amplitude data in the lookup table.

3. The method of claim 2, wherein the lookup table comprises: brain wave frequency data in one or more of alpha, beta, theta, delta, gamma, or mu frequency bands, or any combinations thereof; and corresponding values for the one or more response variables correlating to the brain wave frequency data in one or more of alpha, beta, theta, delta, gamma, or mu frequency bands, or any combinations thereof.

4. The method of claim 2, further comprising adjusting the one or more response variables in the lookup table to recalibrate the lookup table with an input of the user.

5. The method of claim 1, further comprising displaying the one or more response variables in real time.

6. The method of claim 1, further comprising displaying in real time the acquired amplitude data of the acquired brain wave frequency data in one or more frequency bands using one or more brain wave frequency gauges.

7. The method of claim 6, further comprising displaying the acquired amplitude data correlating to the one or more positions of the one or more embedded flags of the media segment using the one or more brain wave frequency gauges.

8. The method of claim 1, further comprising displaying the acquired amplitude data of the acquired brain wave frequency data in time-correlation with the displaying of the media segment.

* * * * *